US011564639B2

(12) United States Patent
Tichauer et al.

(10) Patent No.: US 11,564,639 B2
(45) Date of Patent: Jan. 31, 2023

(54) METHOD AND APPARATUS FOR MEDICAL IMAGING USING DIFFERENCING OF MULTIPLE FLUOROPHORES

(71) Applicant: The Trustees of Dartmouth College, Hanover, NH (US)

(72) Inventors: Kenneth Tichauer, Chicago, IL (US); Robert W. Holt, Lebanon, NH (US); Frederic Leblond, Montreal (CA); Pablo Valdes, Hanover, NH (US); Brian W. Pogue, Hanover, NH (US); Keith D. Paulsen, Hanover, NH (US); David W. Roberts, Lyme, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 829 days.

(21) Appl. No.: 14/767,836

(22) PCT Filed: Feb. 13, 2014

(86) PCT No.: PCT/US2014/016291
§ 371 (c)(1),
(2) Date: Aug. 13, 2015

(87) PCT Pub. No.: WO2014/127145
PCT Pub. Date: Aug. 21, 2014

(65) Prior Publication Data
US 2015/0374308 A1    Dec. 31, 2015

Related U.S. Application Data

(60) Provisional application No. 61/764,506, filed on Feb. 13, 2013.

(51) Int. Cl.
*A61B 5/00*    (2006.01)
*A61K 49/00*   (2006.01)

(52) U.S. Cl.
CPC .......... *A61B 5/7278* (2013.01); *A61B 5/0071* (2013.01); *A61K 49/0058* (2013.01);
(Continued)

(58) Field of Classification Search
CPC ................ A61B 5/7278; A61B 5/0071; A61B 5/0062; A61B 5/0035; A61B 2576/00; A61B 5/0073; A61K 49/0058
See application file for complete search history.

(56) References Cited

U.S. PATENT DOCUMENTS 5,109,276 A    4/1992 Nudelman et al.
6,175,759 B1   1/2001 Chan et al.
(Continued)

FOREIGN PATENT DOCUMENTS

JP    2006-195240 A    7/2006
KR    10-1088364 B1    12/2011
(Continued)

OTHER PUBLICATIONS

Pogue, B. W., Samkoe, K. S., Hextrum, S. K., O'Hara, J. A., Jermyn, M., Srinivasan, S., & Hasan, T. (2010). Imaging targeted-agent binding in vivo with two probes. Journal of biomedical optics, 15(3), 030513. (Year: 2010).*
(Continued)

*Primary Examiner* — Carolyn A Pehlke
*Assistant Examiner* — Johnathan Maynard
(74) *Attorney, Agent, or Firm* — Lathrop GPM LLP

(57) ABSTRACT

A method of generating corrected fluorescence data of concentrations of a targeted fluorophore in tissue of a subject includes administering first and second fluorescent contrast agents to the subject, the first contrast agent targeted to tissue of interest, the second agent untargeted. The tissue is illuminated with light of a first stimulus wavelength and first data is acquired at an appropriate emissions wavelength; the
(Continued)

tissue is illuminated at a second stimulus wavelength and second data is acquired at a second emissions wavelength associated with the second agent, the first and second emissions wavelength differ. Difference data is generated by subtracting the second data from the first data. A system provides for stimulus and capture at multiple wavelengths, with image storage memory and subtraction code, to perform the method. Corrected data may form an fluorescence image, or is used to generate fluorescence tomographic images.

4 Claims, 4 Drawing Sheets

(52) U.S. Cl.
CPC .......... *A61B 5/0035* (2013.01); *A61B 5/0062* (2013.01); *A61B 2576/00* (2013.01)

(56) References Cited

U.S. PATENT DOCUMENTS

| | | |
|---|---|---|
| 6,208,886 B1 | 3/2001 | Alfano et al. |
| 6,661,571 B1 | 12/2003 | Shioda et al. |
| 6,678,398 B2 | 1/2004 | Wolters et al. |
| 6,793,350 B1 | 9/2004 | Raskar et al. |
| 7,387,802 B2 | 6/2008 | Sambanthamurthi et al. |
| 7,804,075 B2 | 9/2010 | Ntziachristos et al. |
| 7,945,077 B2 | 5/2011 | Demos |
| 8,406,859 B2 | 3/2013 | Zuzak et al. |
| 8,948,851 B2 | 2/2015 | Leblond et al. |
| 9,336,592 B2 | 5/2016 | Fan et al. |
| 2002/0099295 A1 | 7/2002 | Gil et al. |
| 2003/0158470 A1 | 8/2003 | Wolter et al. |
| 2004/0015062 A1 | 1/2004 | Ntziachristos et al. |
| 2005/0085732 A1 | 4/2005 | Sevick-Muraca et al. |
| 2005/0111758 A1 | 5/2005 | Lange et al. |
| 2005/0215911 A1 | 9/2005 | Alfano et al. |
| 2006/0024390 A1 | 2/2006 | Schauss et al. |
| 2006/0118742 A1* | 6/2006 | Levenson ............ G01N 21/763 250/559.3 |
| 2007/0038126 A1 | 2/2007 | Pyle et al. |
| 2007/0083124 A1 | 4/2007 | Ehben et al. |
| 2007/0145136 A1 | 6/2007 | Wiklof et al. |
| 2007/0165927 A1 | 7/2007 | Muradyan et al. |
| 2007/0236514 A1 | 10/2007 | Agusanto et al. |
| 2007/0238957 A1 | 10/2007 | Yared |
| 2007/0299335 A1 | 12/2007 | Declerck |
| 2008/0218727 A1 | 9/2008 | Djeziri et al. |
| 2008/0267472 A1 | 10/2008 | Demos |
| 2009/0021746 A1 | 1/2009 | Toida et al. |
| 2009/0036902 A1 | 2/2009 | Dimaio et al. |
| 2009/0137908 A1 | 12/2009 | Patwardhan |
| 2009/0295910 A1 | 12/2009 | Mir et al. |
| 2009/0326362 A1 | 12/2009 | Carlse et al. |
| 2010/0019170 A1 | 1/2010 | Hart et al. |
| 2010/0085423 A1 | 4/2010 | Lange |
| 2010/0106013 A1* | 4/2010 | Morishita .......... G01N 21/6456 600/431 |
| 2010/0145416 A1 | 6/2010 | Kang et al. |
| 2010/0201789 A1 | 8/2010 | Yahagi |
| 2011/0102549 A1 | 5/2011 | Takahashi |
| 2011/0128352 A1 | 6/2011 | Higgins et al. |
| 2011/0175910 A1 | 7/2011 | Yahagi |
| 2011/0183370 A1 | 7/2011 | Noiseux et al. |
| 2011/0222757 A1 | 9/2011 | Yeatman et al. |
| 2011/0275932 A1* | 11/2011 | Leblond ............... A61B 5/0062 600/425 |
| 2011/0293142 A1 | 12/2011 | Van Der Mark et al. |
| 2012/0002012 A1 | 1/2012 | O'Grady et al. |
| 2012/0112098 A1 | 5/2012 | Hoyt |
| 2012/0133740 A1 | 5/2012 | Klimov et al. |
| 2012/0307056 A1 | 12/2012 | Zuzak et al. |
| 2013/0012794 A1 | 1/2013 | Zeng et al. |
| 2013/0038689 A1 | 2/2013 | McDowall |
| 2013/0076863 A1 | 3/2013 | Rappel |
| 2013/0259805 A1 | 10/2013 | Bacskai |
| 2014/0063241 A1 | 3/2014 | Li et al. |
| 2014/0362186 A1 | 12/2014 | Ji et al. |
| 2014/0378843 A1 | 12/2014 | Valdes et al. |
| 2015/0264340 A1 | 9/2015 | Seidl et al. |

FOREIGN PATENT DOCUMENTS

| | | |
|---|---|---|
| WO | 2000/027131 A2 | 5/2000 |
| WO | 2005/089637 A2 | 9/2005 |
| WO | 2007/111570 A2 | 10/2007 |
| WO | 2009/061425 A1 | 5/2009 |
| WO | 2010/090673 A1 | 8/2010 |
| WO | WO 2011/113162 | 9/2011 |
| WO | 2016/007734 A1 | 12/2011 |
| WO | 2013/103870 A1 | 7/2013 |
| WO | 2013/109966 A1 | 7/2013 |
| WO | 2013/116694 A1 | 8/2013 |
| WO | 2013/122710 A1 | 8/2013 |
| WO | 2015/023990 A1 | 2/2015 |
| WO | 2015/187620 A1 | 12/2015 |

OTHER PUBLICATIONS

Tichauer, K. M., Samkoe, K. S., Sexton, K. J., Gunn, J. R., Hasan, T., & Pogue, B. W. (2012). Improved tumor contrast achieved by single time point dual-reporter fluorescence imaging. Journal of biomedical optics, 17(6), 066001. (Year: 2012).*

Tichauer, K. M., Holt, R. W., El-Ghussein, F., Davis, S. C., Samkoe, K. S., Gunn, J. R., . . . & Pogue, B. W. (2013). Dual-tracer background subtraction approach for fluorescent molecular tomography. Journal of biomedical optics, 18(1), 016003. (Year: 2013).*

Tichauer, K. M., Holt, R. W., Samkoe, K. S., El-Ghussein, F., Gunn, J. R., Jermyn, M., . . . & Pogue, B. W. (2012). Computed tomography-guided time-domain diffuse fluorescence tomography in small animals for localization of cancer biomarkers. JoVE (Journal of Visualized Experiments), (65), e4050. (Year: 2012).*

Bradley et al., "A review of attenuation correction techniques for tissue fluorescence", Journal of the Royal Society Interface, vol. 3, Issue 6, Feb. 22, 2006, pp. 1-13.

U.S. Appl. No. 14/373,443; Office Action dated Nov. 16, 2016 (17 pgs).

Fan et al. (Mar. 2, 2011) "Simulation of brain tumor resection in image-guided neurosurgery," Proc. SPIE. vol. 7964. pp. 1-11.

Joshi et al. (2010) "DigiWarp: a method for deformable mouse atlas warping to surface topographic data," Phys. Med. Biol. 55(20):6197-6214.

Najib et al. (Apr. 2011) "Transcranial Brain Stimulation: Clinical Applications for Future Directions," Neurosurg. Clin. N. Am. 22(2):233-251.

Patwardhan (2005) "Monte Carlo Simulation of Light-Tissue Interaction: Three-Dimensional Simulation for Trans-Illumination-Based Imaging of Skin Lesions," IEEE Transactions on Biomedical Engineering. 52(7):1227-1236.

Sun et al. (2005) "Stereopsis-guided brain shift compensation," IEEE Trans. Med. Imaging. 25(8):1039-1052.

Tichauer et al. (2003) "Dual-tracer background subtraction approach for fluorescent molecular tomography," Journal of Biomedical Optics. 18(1):016003. pp. 1-11.

Tichauer et al. (Apr. 17, 2014) "Accounting for pharmacokinetic differences in dual-tracer receptor density imaging," Phys. Med. Biol. 59:2341-2351.

Tichauer et al. (Jun. 2012) "Improved tumor contrast achieved by single time point dual-reporter fluorescence imaging," Journal of Biomedical Optics. 17(6):066001. pp. 1-10.

Valdes et al. (Jun. 1, 2012) "A spectrally constrained dual-band normalization technique for protoporphyrin IX quantification in fluorescence-guided surgery," Optics Letters. 37(11):1817-1819.

Vigneron et al. (2009) "2D XFEM-Based Modeling of Retration and Successive Resections for Preoperative Image Update," Comput. Aided Surg. 14(1-3):1-20.

(56) References Cited

OTHER PUBLICATIONS

International Search Report with Written Opinion corresponding to International Patent Application No. PCT/US2009/066839, dated Jun. 25, 2010.
International Search Report with Written Opinion corresponding to International Patent Application No. PCT/US2013/020352, dated Apr. 26, 2013.
International Search Report with Written Opinion corresponding to International Patent Application No. PCT/US2013/022266, dated May 15, 2013.
International Search Report with Written Opinion corresponding to International Patent Application No. PCT/US2013/024400, dated May 15, 2013.
International Search Report with Written Opinion corresponding to International Patent Application No. PCT/US2014/016291, dated May 27, 2014.
International Search Report with Written Opinion corresponding to International Patent Application No. PCT/US2014/051356, dated Dec. 9, 2014.
International Search Report with Written Opinion corresponding to International Patent Application No. PCT/US2015/033672, dated Aug. 19, 2015.
International Search Report with Written Opinion corresponding to International Patent Application No. PCT/US2015/039728, dated Oct. 7, 2015.
Notice of Allowance corresponding to U.S. Appl. No. 13/145,505, dated Sep. 30, 2014.
Notice of Allowance corresponding to U.S. Appl. No. 14/370,713, dated May 18, 2016.
Notice of Allowance corresponding to U.S. Appl. No. 14/375,311, dated Jan. 20, 2016.
Office Action corresponding to U.S. Appl. No. 13/145,505, dated Jun. 20, 2013.
Office Action corresponding to U.S. Appl. No. 14/370,713, dated Feb. 2, 2016.
Final Rejection in U.S. Appl. No. 14/373,443 dated Jun. 21, 2017, 20 pp.
Saager et al., "Quantitative fluorescence imaging of protoporphyrin IX through determination of tissue optical properties in the spatial frequency domain", Journal of Biomedical Optics, Dec. 2011, vol. 16, Issue 12, pp. 1-5.
Zhang et al., "Turbidity-free fluorescence spectroscopy of biological tissue", Optic Letters, Oct. 1, 2000, vol. 25, Issue 19, pp. 1451-1453.
Raymond et al. (2010) "Lifetime-based tomographic multiplexing," Journal of Biomedical Optics, vol. 15, Issue 4, 9 pp.
U.S. Appl. No. 14/373,443, Final Office Action dated Dec. 17, 2018, 26 pp.

\* cited by examiner

METHOD AND APPARATUS FOR MEDICAL IMAGING USING DIFFERENCING OF MULTIPLE FLUOROPHORES

RELATED APPLICATIONS

The present application claims priority to U.S. Provisional Patent application 61/764,506 filed 13 Feb. 2013.

The application is also related to the subject matter of PCT/US13/24400 filed Feb. 1, 2013, which claims priority to U.S. Provisional patent application 61/594,862 filed Feb. 3, 2012.

This application is also related to PCT Patent Application Serial No. PCT/US13/20352 filed 4 Jan. 2013, which claims priority to U.S. Patent Application Ser. No. 61/583,092, filed Jan. 4, 2012.

This application is also related to U.S. patent application Ser. No. 13/145,505, filed in the United States Patent and Trademark Office on Jul. 20, 2011, which is a U.S. National Phase application of PCT Patent Application PCT/US09/66839 filed Dec. 4, 2009, which claims priority to U.S. Provisional Patent Application 61/145,900.

This application is also related to PCT Patent Application Serial No. PCT/US13/22266 filed Jan. 18, 2013, which claims priority to U.S. Provisional Application Ser. No. 61/588,708, filed Jan. 20, 2012. The disclosures of the above-referenced applications are incorporated herein by reference.

GOVERNMENT INTEREST

This invention was made with government support under grant numbers R01 CA109558, K25 CA138578, and R01 CA120368 awarded by the National Institutes of Health. The government has certain rights in the invention.

BACKGROUND

Fluorescence-based medical imaging has been proposed for detecting and mapping tumor, and other abnormal, tissues in organs such as, but not limited to, breast and brain; in particular fluorescence-based imaging is believed to be useful in identifying abnormal tissues during surgery so that a surgeon may remove more abnormal tissue while avoiding damage to nearby normal tissues.

A fluorophore is a compound, synthetic (like Fluorescein), naturally occurring, a byproduct of metabolism of a prodrug, or, like Protoporphyrin IX, both naturally occurring in tissue and a byproduct of metabolism of a prodrug, that may be present in mammalian tissue. Each molecule of fluorophore has the ability to absorb one or more photons of light of a first, or stimulus, wavelength, thereby raising the molecule to an excited energy state; the molecule may then drop to another energy state by emitting at least one photon of light at one or more second, or emission, wavelengths. The stimulus wavelength is typically shorter than the emissions wavelength. The stimulus and emissions wavelengths may be in the ultraviolet, visible, or infrared portions of the spectrum.

Typical fluorescence-based medical imaging systems have an imaging optical system adapted to focus light at the emissions wavelength onto a photodetector array. Such systems have a stimulus light source that provides light that includes the stimulus wavelength but excluding the emissions wavelength. The stimulus light source may be a laser, a light-emitting diode, or a lamp, typically combined with a stimulus wavelength-selective device such as a band-pass filter for eliminating stray emissions-wavelength light. The stimulus light source is arranged to provide light to the tissue, in some systems directly and in others through lenses of the optical system. Typically, the optical system has a receiving wavelength-selective device, such as a long-wavelength-pass receiving filter that blocks light at the stimulus wavelength, for excluding stimulus light from the detector while allowing fluorescence emissions-wavelength light reach the detector. Images captured from the photodetector array typically are processed by an imaging processing system, and prepared for presentation on a display system.

Systems are known that can be adapted for fluorescence-based imaging of different fluorophores. In typical systems, both the stimulus wavelength-selective device and the receiving wavelength-selective device are replaceable to adapt the system for use with different fluorophores. In one such system type, both stimulus and receiving wavelength-selective devices are on rotary disk mounts that may have a clear or neutral-density device in a different position on the disk than the receiving device, such that white light images may also be obtained. In a particular embodiment, a stimulus-filter disk has filters adapted for white light and two or more stimulus filters, with each stimulus filter adapted for operation with a different fluorophore; similarly the receiving-filter disk has filters adapted for white light and two or more receive filters, with each receive filter adapted for operation with a different fluorophore. In other systems, separate stimulus light sources may be provided for white light imaging and for use with each desired fluorophore.

Existing fluorescence-based imaging systems often suffer from a lack of contrast, in part because some normal tissue constituents are fluorophores, and in part because fluorophores administered as contrast agents to tissue are concentrated in tissue to varying degrees. In particular, some exogenous fluorophores bound to tissue-selective molecules, such as antibodies, may merely be more strongly retained by abnormal than normal tissues, leaving a substantial background level of fluorophore in normal tissue that may obscure visibility of fluorophore concentrations in abnormal tissue.

Diffuse-optical fluorescence tomography (FTI) systems are known. In order to reconstruct a three-dimensional model of fluorescent emissions in tissue, these systems typically are adapted to acquire either a sequence of images, or a sequence of light emissions data at specific points on a surface of the tissue, with each image or light emissions datum captured with light applied to different points on the tissue surface either by scanning a light source or by applying stimulus wavelength light sequentially through optical fibers and optodes positioned at specific points on tissue surface. These systems typically construct a voxel-based three dimensional model of light propagation and fluorescent emissions in the tissue and solve for light scattering, absorbance, and fluorophore concentration at each voxel. Voxel-based modeling and parameter reconstructions require good contrast in images for proper reconstruction.

Planar fluorescent imaging (PFI) and FTI are useful in physiological studies of small animals, and in the diagnosis and treatment of various lesions, including malignant lesions of the breast, in larger organisms including humans.

SUMMARY

It is desirable to enhance contrast in fluorescence imaging, in both planar and tomographic systems, and to provide improved discrimination between tissue types, including abnormal and normal tissue types.

A method of generating corrected fluorescence data of concentrations of a targeted fluorophore in tissue of a subject, includes administering first and second fluorescent contrast agents to the subject, the first contrast agent targeted to tissue of interest, and the second agent untargeted. The tissue is then illuminated by light of a first stimulus wavelength and first data is acquired at a first emissions wavelength associated with the first agent; the tissue is then illuminated at a second stimulus wavelength and second data is acquired at a second emissions wavelength associated with the second agent, where the first and second emissions wavelength differ. Corrected data is generated by subtracting the second data from the first data. A system is configured with stimulus and capture at multiple wavelengths, with image storage memory and subtraction code, to perform the method. Corrected data may form a fluorescence image, or be used to generate fluorescence tomographic images.

In alternative embodiments, both tracers are stimulated simultaneously by combining multiple stimulus wavelengths and using intelligent emission filtering to distinguish concentration of the fluorophores from differences in emission spectra associated with each fluorophore, and in some embodiments both contrast agents are stimulated by a single illumination source if the agents have significantly different emission spectrums.

In an embodiment, a method of generating corrected fluorescence data of concentrations of a targeted fluorophore in tissue of a subject, includes administering a first fluorescent contrast agent to the subject, the first contrast agent also selected from the group consisting of tissue-targeted agents containing the targeted fluorophore and agents containing a tissue-targeted prodrug metabolizable into the targeted fluorophore; administering a second fluorescent contrast agent to the subject, the second contrast agent non-tissue-targeted and containing a second fluorophore; illuminating tissue of the subject with light of a first stimulus wavelength; acquiring first data at a first emissions wavelength associated with the first fluorophore; acquiring second data at a second emissions wavelength associated with the second fluorophore, the second emissions wavelength differing from the first emissions wavelength; and subtracting the second data from the first data to provide the corrected fluorescence data.

An embodiment includes a system for generating corrected fluorescence data of concentrations of a targeted fluorophore in tissue of a subject, having apparatus for generating and illuminating tissue with light of a first stimulus wavelength; apparatus for generating and illuminating tissue with light of a second stimulus wavelength; photodetector apparatus adaptable to capture first data at a first emissions wavelength, and to capture second data at a second emissions wavelength; a memory configured to store first data and second data; a processor configured with machine readable code in the memory to scale at least one of first and second data, and to generate corrected data by subtracting the second data from first data.

DETAILED DESCRIPTION OF THE EMBODIMENTS

Figure 1:
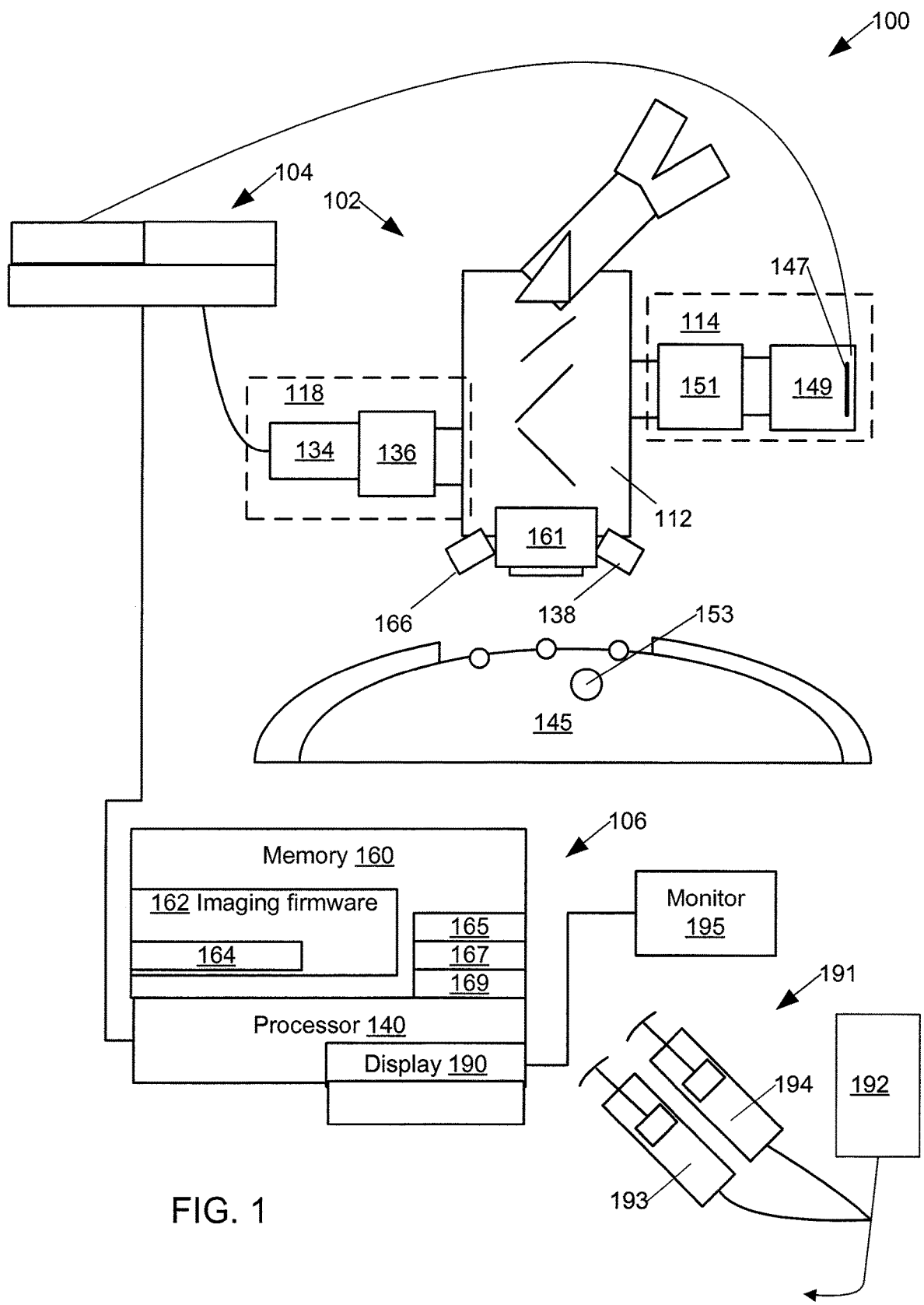
FIG. 1 is a block diagram of a fluorescent imaging system, in an embodiment.
Figure 2:
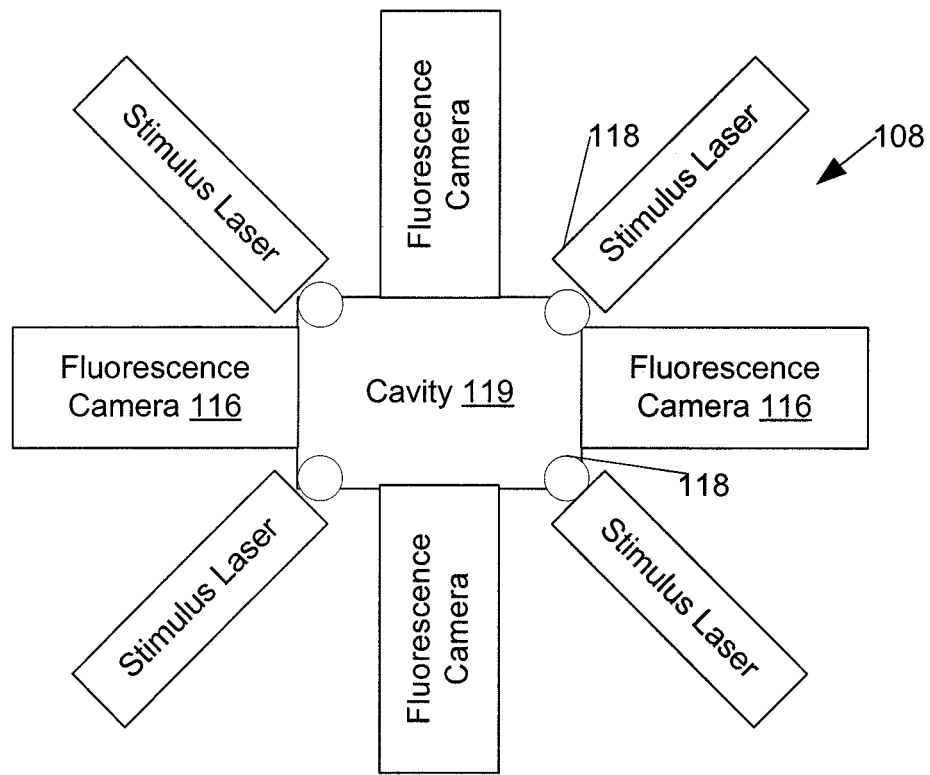
FIG. 2 is a block diagram of an optical subsystem with scanned stimulus lasers and sensing cameras of an alternative embodiment of a fluorescent imaging system.
Figure 2A:
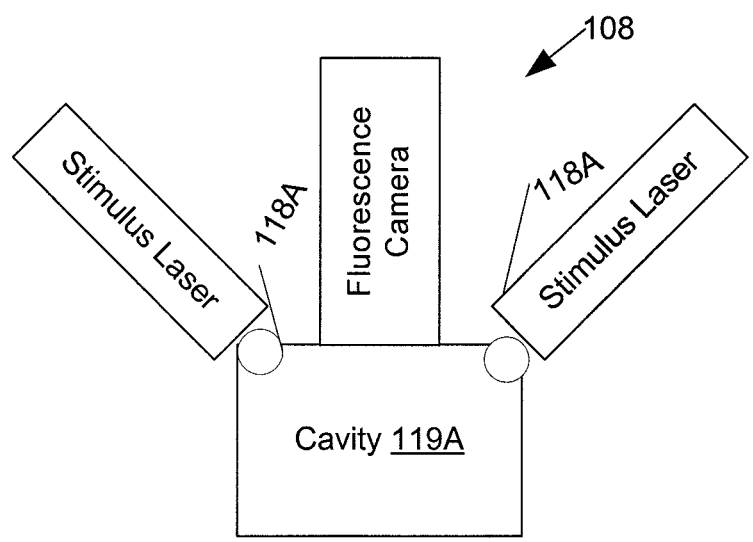
FIG. 2A is a block diagram of an optical subsystem with scanned stimulus lasers and sensing cameras of another alternative embodiment of a fluorescent imaging system.
Figure 3:
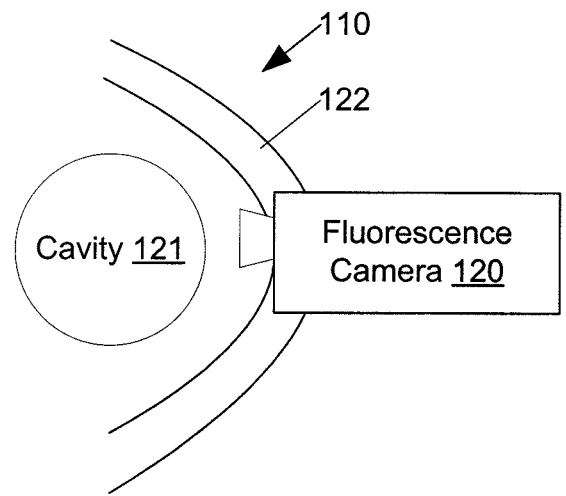
FIG. 3 is a block diagram of an optical subsystem with stimulus and sensing hardware of another alternative embodiment of a fluorescent imaging system.

A fluorescent imaging system 100 (FIG. 1) has an optical subsystem 102, 108, 110, 109 (FIG. 1, 2, 3, or 4) an interface subsystem 104, and an image processing system 106. In various embodiments, the optical subsystem 102 may be integrated with a surgical microscope 112 as illustrated in FIG. 1, may have a fluorescence camera 114 integrated with a surgical microscope 112 having a lens subsystem 161, may have multiple fluorescence cameras 116 and scanned-laser stimulus light sources 118, 118A as illustrated in FIG. 2 or 2A, may have a single fluorescence camera 120 mounted on a motorized track 122 as illustrated in FIG. 3, may have multiple laser stimulus light sources 124, 125 coupled through optical fibers 126 and optodes to tissue 128, with additional optodes coupled through fibers 130 to a multi-channel spectrally-selective or spectrographic detector 132 or may have another configuration not shown. It is anticipated that many of the principles described herein are also applicable to both imaging systems similar to that of FIG. 1, and nonimaging, multiple-probepoint diffuse-optical systems resembling that of FIG. 4. The optical system configuration is determined by a particular application of the fluorescent imaging system and a depth in tissue at which it is desired to determine fluorophore concentrations.

Figure 4:
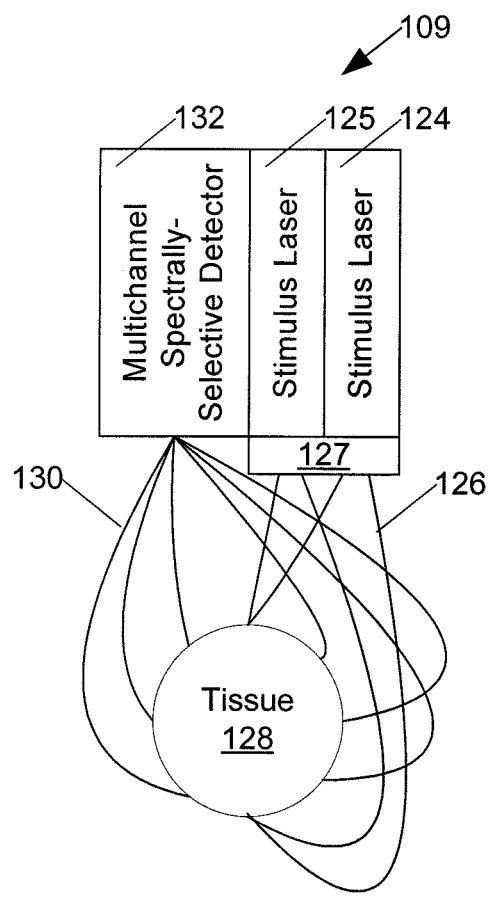
FIG. 4 is a block diagram of an optical subsystem with stimulus and sensing hardware of yet another alternative embodiment of a fluorescent imaging system.

While digital images acquired by a system as illustrated in FIG. 1 may directly represent surface fluorophore concentrations, it is anticipated that machine readable instructions in memory 160 of nonimaging, multiple-probepoint, systems, such as that of FIG. 4, includes machine readable instructions for reconstructing three dimensional models distribution of fluorophore in tissue from data acquired from the detector 132. In certain embodiments, this is done in a manner similar to that of prior diffuse optical imaging systems. This may be done by sequentially illuminating tissue with a stimulus-wavelength light at each of a plurality of locations on tissue through fibers or with a scanning laser, and measuring fluorescent emissions light, and in some embodiments stimulus light, at multiple locations on tissue surface. Then, a voxel-based model of light propagation and fluorescence in tissue, with parameters at each voxel for fluorophore concentration, attenuation, and scattering in the tissue is generated. The model parameters at each voxel are then fit to the measurements of emissions, and in some embodiments stimulus light, to generate a map of fluorophore concentration in tissue.

In each embodiment, stimulus light sources 118, such as stimulus lasers 124, 125, scanned-laser stimulus light source 118A, broadband lamps 134 or white LEDs operating in conjunction with a rotary filter disk 136, or colored LEDs 138, are controlled through interface subsystem 104 by processor 140 of image processing system 106. In all embodiments, light from stimulus light sources is coupled directly or indirectly through the optical system to illuminate any tissue in an imaging area, such as tissue 128, 145, or any tissue (not shown) in cavity 119, 121. Tissue 128, 145, or any tissue (not shown) in cavity 119, 121, may have an included nonhomogenicity such as a tumor 153.

In each embodiment, light, including emissions light, from tissue 128, 145, or any tissue (not shown) in cavity 119, 121, is imaged or detected by a detector, such as multichannel spectrally-selective or spectrographic detector 132, or fluorescence cameras 114, 116, 120. Each fluorescence camera has a broadband photodetector array 147 in an electronic camera 149 that is configured to receive light from tissue or the optical system through a lens and a rotary filter disk 151. Signals from fluorescence cameras or photodetectors of each imaging system are received through interface subsystem 104 into image processing system 106. A particular multichannel spectrographic detector embodiment has an N-channel spectrographic detector using an N by M photodetector array circuit. In this embodiment, light received from a sensing line across tissue is admitted through a spectrally dispersive device such as a prism or diffraction grating, such that light from each of N points, or pixels, along the sensing line is spread by wavelength across M photodetectors of the Nth row or column of the detector array. A scanning mirror is configured to scan the line across a field of view of the optical system to provide an image with spectrographic data at each pixel of the image.

Image processing system 106 has a memory 160 coupled to processor 140, the memory 160 configured with machine readable code of fluorescence imaging routines 162. The fluorescence imaging routines include routines 164 for performing a multiple-tracer background-subtraction image-processing procedure as discussed below. In at least a first mode, the multiple-tracer background-subtraction image-processing routines are configured to perform the following:
  a) using the stimulus light sources 118, 118A illuminate tissue with a first predetermined stimulus wavelength;
  b) using the fluorescence camera 114, 116, obtain a first image or data at at least a first fluorescence wavelength;
  c) using the stimulus light sources 118, 118A illuminate tissue with a second predetermined stimulus wavelength;
  d) using the fluorescence camera 114, 116, obtain a second image or data at at least a second fluorescence wavelength;
  e) scale one or more of the first and second images or data such that background fluorescence may be eliminated by differencing the first and second images; and
  f) difference the first and second images to produce a difference image.

The system also incorporates drug or prodrug administration apparatus 191, which in an embodiment includes an intraveinous solution supply 192, a first syringe 193, syringe-pump, or other solution dispensing device, an optional second syringe 194 or syringe-pump, and associated IV tubing and catheters such that an agent in the first and second syringe may be administered to a subject. In an embodiment, a first fluorescent contrast agent utilizing a first fluorophore or a prodrug metabolized to the first fluorophore is provided in the first syringe, and a second fluorescent contrast agent utilizing a second fluorophore is provided in the second syringe, or in other embodiments is mixed with the first contrast agent in the first syringe.

The first and second fluorophores are chosen such that they may be readily distinguished. In an embodiment. the first and second fluorophores have different fluorescent emissions wavelengths and the system is configured such that the first emissions wavelength is an emissions wavelength of the first fluorophore, and the second wavelength is an emissions wavelength of the second fluorophore. The first stimulus wavelength is chosen to optimize imaging of concentrations of the first fluorophore in tissue, and the second stimulus wavelength is chosen to optimize imaging of concentrations of the second fluorophore in tissue; in many embodiments the first and second stimulus wavelengths are different. In an alternative embodiment, the first and second fluorophores are distinguishable because they have different peak stimulus wavelengths, in this embodiment the first stimulus wavelength is chosen to optimize imaging of concentrations of the first fluorophore in tissue while minimizing imaging of the second fluorophore, and the second stimulus wavelength is chosen to optimize imaging of concentrations of the second fluorophore in tissue while minimizing imaging of the first fluorophore.

In some embodiments, the first fluorophore is a product of metabolism of a prodrug in tissue, such as protoporphyrin IX produced from 5-aminolevulinic acid (ALA), in other embodiments the first fluorophore is a fluorescent substance.

In an embodiment, the first and second contrast agents are chosen to have differing affinity to at least one tissue type in tissue 145, in some such embodiments the first agent may be a fluorescent-labeled antibody to a protein associated with tumor 153 such that the first agent will concentrate in tumor 153 relative to surrounding tissue. In these embodiments, the second agent is chosen such that it does not concentrate in tumor 153 to the same extent as the first agent. In other embodiments, the first agent is a prodrug metabolized in tissue to first fluorophore at a different rate in tumor 153 than in surrounding normal tissue.

Figure 5:
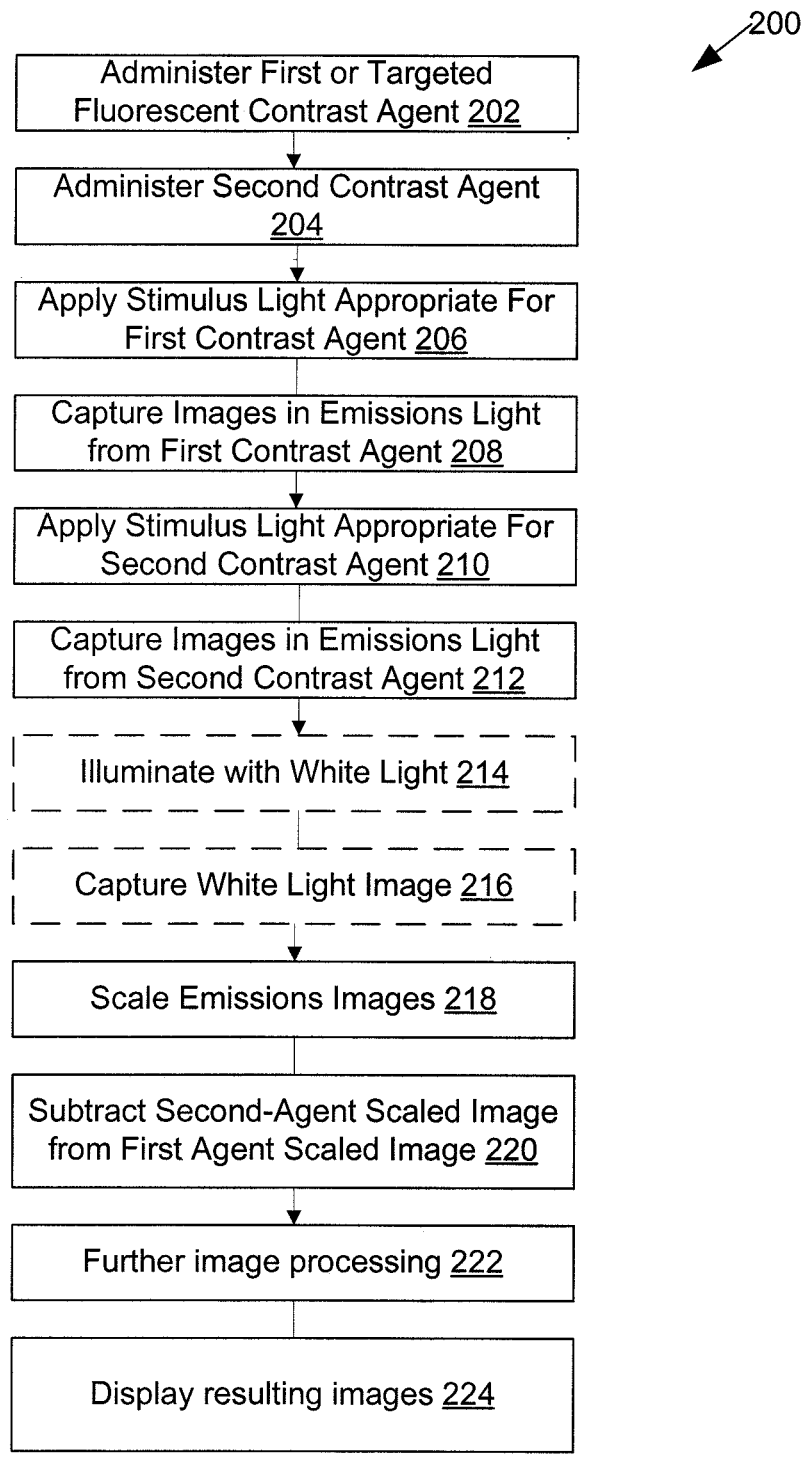
FIG. 5 is a flowchart of a method for contrast enhancement for a fluorescent imaging system, in an embodiment.

The system is operated according to the method 200 of FIG. 5. A first contrast agent is administered 202 to a subject, typically by injection from administration apparatus 191 into a blood vessel such that the contrast agent is transported to tissue 128, 145, or tissue (not shown) that may be in cavity 119, 121. A second contrast agent is also administered 204 to the subject. In a particular embodiment, the first and second contrast agents are mixed, optionally in a single syringe, such as first syringe 193, and injected simultaneously into the same blood vessel. One of these contrast agents such as the second agent, may be a nonselective fluorescent agent containing a second fluorophore, the other agent, such as the first agent, is a selective fluorescent agent such as an antibody tagged with a first fluorophore that concentrates in particular types of tissue, such as tumor 153. In an alternative embodiment, the first agent is a prodrug, such as 5-aminolevulinic acid (5-ALA) that is metabolized in tissue into a first fluorophore such as protoporphyrin IX. Sufficient time is allowed after administration of the first agent for the first agent to concentrate in tissue, or for the prodrug to be metabolized into the first fluorophore.

Once the fluorophores are in place in tissue 128, 145, or tissue (not shown) that may be in cavity 119, 121, processor 140 operating under control of imaging routines 162 triggers illumination 206 of the tissue with light of a first stimulus wavelength suitable for inducing emitted light from the first fluorophore. In doing so, processor 140 turns on a first stimulus illuminator, such as laser 124. In other embodiments, processor 140 rotates rotary filter disk 136 to position a filter suitable for passing light of the first stimulus wavelength in front of lamp 134 and activates the lamp 134. The processor 140 operating under control of imaging routines 162 also adjusts rotary filter-changers, such as filter 151, of the fluorescent cameras 114, 116, or 120, to a filter that blocks light of the first stimulus wavelength but passes light of a first emitted wavelength that may be emitted by the first fluorophore.

While light of the first stimulus wavelength illuminates the tissue, light of the first emitted wavelength from the first fluorophore is captured by the optical system and capture or imaged 208 by fluorescent cameras 114, 116, 120, or captured 208 by multichannel spectrally-selective or spectrographic detector 132. Images from the cameras, or data from the detector, is passed through interface subsystem 104 into processing system 106, where it is stored as a first-fluorophore image 165 or, in nonimaging systems, a first reconstructed three-dimensional model of fluorophore distribution.

Processor 140 operating under control of imaging routines 162 then triggers illumination 210 of the tissue with light of a second stimulus wavelength suitable for inducing emitted light from the second fluorophore. In doing so, processor 140 may turn on a second stimulus illuminator, such as laser 125. In other embodiments, processor 140 rotates rotary filter disk 136 to position a filter suitable for passing light of the second stimulus wavelength in front of lamp 134 and activates the lamp 134. The processor 140, operating under control of imaging routines 162, also adjusts rotary filter-changers, such as filter 151, of the fluorescent cameras 114, 116, or 120, to a filter that blocks light of the second stimulus wavelength but passes light of a second emitted wavelength that may be emitted by the second fluorophore.

While light of the second stimulus wavelength illuminates the tissue, light of the second emitted wavelength from the second fluorophore is captured 212 by the optical system and imaged by fluorescent cameras 114, 116, 120, or captured by multichannel spectrally-selective or spectrographic detector 132. Images from the cameras, or data from the detector, is passed through interface subsystem 104 into processing system 106, where it is stored as a second-fluorophore image 167, or, in nonimaging embodiments, a second three-dimensional model of fluorophore distribution.

In an alternative embodiment, the first and second stimulus wavelength may be the same, however the first and second emitted wavelengths must then differ to permit distinguishing emitted light from the first and second fluorophores.

In some embodiments, a third, white-light, illuminator 166, may be activated, or a filter of rotary filter-changer 136 is rotated to a neutral-density filter to illuminate 214 the tissue with white light. Similarly, filter 151 of the camera is rotated to a neutral density filter; a white-light image is then captured 216.

One or both of the first (selective) fluorophore image 165 and second (nonselective) fluorophore image 167 are scaled 218 such that the intensity of background in the first image approximately matches intensity of the second image, the second image is then subtracted 220 from the first image to form a corrected or difference image 169, or, in nonimaging embodiments, a corrected three dimensional model of targeted fluorophore concentrations. The scaling compensates for differences in overall concentration of the two fluorophores, as well as differences in stimulus wavelength intensity, fluorescent photon efficiency, and other factors.

In fluorescent tomographic applications, typically those having the optical system of FIG. 2 or 4 although other configurations are anticipated, the difference image 169 is then used in further processing 222 to reconstruct tomographic images of the tissue. In planar imaging applications, typically having an optical system of FIG. 1 or 3 although other configurations are anticipated, the corrected image or dataset may be color-coded and superimposed on white light images by superimposed processing routines in memory 160 to assist a surgeon in locating fluorophore concentrations in tissue, or otherwise processed. Resulting images are then displayed 224 on a monitor 195.

Results with Fluorescent Tomography

In a particular Fluorescent Tomography (FT) embodiment having laser stimulus illuminators, and an optical system resembling that of FIG. 4, one laser was configured at a wavelength of 635 nm and the other configured at a wavelength of 755 nm. The lasers were pulsed at 40 MHz, 180 degrees out of phase from each other. Each laser beam was passed through a 10-nm band-pass filter centered at the respective wavelengths of the lasers to eliminate stray light at other wavelengths, before both beams were coupled into stimulus optical fibers for illuminating tissue, and through a distributor 127 such that the lasers illuminate stimulus fibers individually.

The embodiment was tested with phantom having a first contrast agent having first fluorophore concentrated in an inclusion, with a background level of first fluorophore in the remainder of the phantom with a 4:1 contrast ratio between the inclusion and background. A second contrast agent containing a second fluorophore as present throughout the phantom.

The embodiment was also tested with a mouse model, each mouse having a culture human glioma growing on it. With the mouse model, the first, selective, contrast agent was a tagged fluorescent agent targeting epidermal growth factor receptors (EGFR) IRDye 800CW-EGF from LI-COR Biosciences, Lincoln, Nebr. The second, nonselective, contrast agent was Alexa Fluor 647 from Life Technologies, Grand Island, N.Y., with its ester binding site inactivated; in an alternative embodiment Alexa Fluor 750 from the same source was used as the second, nonselective, fluorophore. The agents were administered to the mouse.

Data was captured by the multichannel spectrally-selective or spectrographic detector 132 using the phantom at first and second fluorophore emission wavelengths with the phantom illuminated through each optical fiber 126. The first fluorophore data was corrected by subtracting scaled data taken of the second fluorophore as herein described to provide corrected data.

Fluorescent tomographic images of the inclusion were successfully reconstructed from the corrected data by constructing a voxel-based model having parameters for fluorophore concentration, light scattering, and light emissions at each voxel, and fitting these parameters to the corrected data; images are then generated by mapping voxels to pixels of an image. Similarly, data was captured from tissue of the mouse at first and second fluorophore emission wavelengths, corrected as described, and tomographic images of the mouse successfully resolving the glioma were constructed.

One or both of the first (selective) fluorophore image 165 and second (nonselective) fluorophore image 167 are scaled 218 such that the intensity of background in the first image approximately matches intensity of the second image, the second image is then subtracted 220 from the first image to form a corrected image or dataset 169 to form a corrected image of targeted fluorophore concentrations.

In fluorescent tomographic applications, the corrected image or dataset 169 is then used in further processing 222 to reconstruct tomographic images of the tissue. In planar imaging applications, typically having an optical system of FIG. 1 or 3 although other configurations are anticipated, the corrected image or dataset may be color-coded and superimposed on white light images or otherwise processed. Resulting images are then displayed 224 on monitor 192.

In the present document, an approach is proposed in which the uptake of a second, untargeted fluorescent tracer can be used to subtract off the non-specific uptake of a simultaneously injected targeted fluorescent tracer. As long as the two tracers have similar delivery characteristics (i.e., their vascular permeability and blood kinetics are similar) and the non-specific fluorescence uptake is much greater than the level of autofluorescence, the untargeted tracer fluorescence data can be used as a scaled surrogate of the non-specific component of the targeted tracer uptake, allowing a means of subtracting off background even if it is heterogeneous or is found in high concentrations in organs of filtration. This development is explored through simulations, phantom experiments, and in a pilot in vivo study.

When exciting fluorescent molecules within a biological tissue, the measurement of reemitted fluorescent light at the surface can be considered to be linear with respect to the fluorophore concentration in the limit that the absorption of the fluorophores is much less than that of the main endogenous absorbers in tissue (including hemoglobin, lipids and water). The dual-tracer background subtraction approach introduced here assumes this linearity hypothesis holds at two wavelengths of interest, namely the excitation wavelengths of (1) a targeted and (2) an untargeted fluorescent tracer. The general mathematical framework for the single-wavelength linear FT inverse problem has been presented elsewhere. Here the methodology of a general dual-wavelength FT problem is presented and solved. If m optical measurements are made and the interrogated spatial domain is discretized into n volume elements (e.g., finite elements or rectilinear voxels), the linear problem can be expressed as a matrix equation mapping the n-by-1 fluorescence yield vector, x; (where i=T represents the notation for data from a targeted tracer and i=U is notation for an untargeted tracer), to the m-by-1 data vector, d, composed of fluorescence measured at select source-detector pair positions on the surface of the imaging domain at targeted and untargeted tracer wavelengths, $\lambda_i$:

$$J_i x_i = d_i. \quad (1)$$

The operator $J_i$ is the m-by-n forward model or sensitivity matrix defined at wavelengths $\lambda_i$. For a given imaging geometry and spatial discretization, and in the diffusion limit, $J_i$ is strictly a function of the light absorption ($\mu 0$) and reduced scattering ($\mu s'$) properties of the imaging medium. These properties vary amongst all n imaging domain elements and are included in the vector $\mu_i$: i.e., $$J_i = J(\mu_i), \quad (2)$$

To understand the utility of the untargeted tracer distribution as a means of removing unwanted background signal from a targeted tracer distribution (and potentially other factors unaccounted for through modeling), the vectors $X_T$ and $X_U$, representing the targeted and untargeted tracer distributions, respectively, can be expanded as follows:

$$X_T = X_{bound} + X_{bk} + X_{af}$$

$$X_U = X_{bk,u} + X_{af,u}, \quad (3)$$

where the vector $X_{bound}$ represents the amount of targeted fluorophore bound to its specific receptor at each element of the domain, the vector $X_{bk}$ is the amount of unbound or "background" targeted fluorescence at each element of the domain, the vector $X_{af}$ is the amount of autofluorescence (endogenous fluorescence) at the wavelength used to detect the targeted fluorescence, and the vectors $X_{bk,u}$ and $X_{af,u}$ are the corresponding background and autofluorescence distributions at the untargeted tracer wavelength, It should be noted that there is no bound term in xu as a result of the untargeted tracer not being able to bind to the specific receptors of the targeted tracer. If the simultaneously injected untargeted tracer (fluorescing at a different wavelength: typically greater than 50 nm peak-to-peak separation) is assumed to have similar delivery characteristics to the targeted tracer, the background distribution of the targeted tracer can be approximated to be a linear function of the background distribution of the untargeted tracer. For example, mathematically this would be, $X_{bk} = c_1 x_{bk,u}$, where $c_1$ is a constant that accounts for effects such as differences in the system sensitivity at the targeted and untargeted tracer wavelengths and/or differences in quantum efficiency or injected concentration between the two tracers. Similarly, a second hypothesis here is that the autofluorescence at the targeted tracer wavelength can be written as a linear function of the autofluorescence at the untargeted tracer wavelength. This can be mathematically expressed as, $X_{af} = c_2 X_{af,u}$, where $c_2$ is a constant that accounts for differences in the magnitude of autofluorescence at the targeted and untargeted tracer wavelengths. Therefore, Eq. 1 can be re-written at the targeted and untargeted tracer wavelengths as follows:

$$J_T(X_{bound} + X_{bk} + X_{af}) = d_T$$

$$J_U = (x_{bk}/c_1 + x_{af}/c_2) \quad (4)$$

In order to accommodate the forward model matrix difference, a third hypothesis is made that an "average" sensitivity function, $\bar{J}$, can be defined as follows:

$$\bar{J} = J(\bar{\mu}), \quad (5)$$

where $\bar{\mu}$ is the mean of the optical properties in the vectors $\mu_T$ and $\mu_u$. This new sensitivity function is taken to have similar mathematic properties to the matrices $J_T$ and $J_u$ and are used henceforth instead. In addition, the fourth and last hypothesis that is that $X_{af} \ll X_{bk}$ holds at both wavelengths, which is true for systemically injected near-infrared fluorescent tracers at least out to 24 h after injection. If these four hypotheses are accurate, the difference of the two lines in Eq. 4 can be simplified to:

$$\bar{J} X_{bound} = d_T - c_1 d_u \quad (6)$$

The scaling coefficient c (redefined for brevity from $c_1$) is difficult to calculate directly because the quantum efficiencies of the two fluorophores are difficult to know exactly and the sensitivity of the imaging system as a function of wavelength is difficult to characterize. Instead, since most targeted fluorescence tomography applications assume binding will occur only within a set number of inclusions within the imaging domain, it is assumed that for some source-detector pair the relative contribution of bound targeted signal to $d_T$ will be negligible. Assuming this, c can be estimated in the following way:
 1. Find $c_0$ such that $\max(c_0 d_u) \leq 0.1 * \min(d_T)$.
 2. Define $d_{U,test} = 1.01^p c_0 d_U$, where p is a positive integer.
 3. Find maximum p such that $\min(d_T - d_{U,test}) > 0$.
 4. Take $c = 1.01^p c_0$ Thus, a method is provided to build all parts of Eq. 6, save the unknown bound distribution, which is the quantity of interest.

If the background fluorescence is assumed to be relatively homogeneous, then it may not be necessary to employ a second untargeted tracer for the background subtraction. Rather, homogeneous fluorescence background can potentially be removed by substituting a simulated Born-normalized data vector that assumes some level of homogenous fluorescence dispersed throughout the imaging domain in place of du in Eq. 6. Henceforth this approach will be referred to as the homogeneous background subtraction approach.

To test out the dual-tracer background subtraction approach in phantom and animal studies, fluorescence from targeted and untargeted fluorescent tracers was imaged on a microcomputed tomography-guided time-domain fluorescence tomography system. Much of the particulars of the system have been covered in depth previously. A schematic of the dual wavelength version of the system is presented. In brief, the fluorescence tomography system is a non-contact fan-beam geometry system using two pulsed-diode lasers (Picoquant, Berlin, Germany), one centered at 635 nm and the other centered at 755 nm. For the experiments carried out in this study, the lasers were pulsed at 40 MHz, 180° out of phase from each other. Each laser beam was passed through a 10-nm band-pass filter (Chroma Technologies, Bellows Falls, Vt.) centered at the respective wavelengths of the lasers before coupling the beams into separate 50-µm multimode optical fibers (Thorlabs, Newton, N.J.). Tests of the laser demonstrated that the 755 nm laser was more powerful than the 635 nm laser, so as a means of having control over the relative strengths of the two lasers, the output of the 755 nm laser fiber was passed through an in-line motorized variable neutral density filter (OZ Optics, Ottawa, ON), before the optical fibers from both lasers were coupled together into a single 100-µm fiber using a custom-made fiber combiner (OZ Optics, Ottawa, ON). The output of the fiber combiner was then passed through a second variable neutral density filter, to control the overall excitation power of the system, and then separated into two fibers using a 96/4 in-line beamsplitter (OZ Optics, Ottawa, ON). The 4% output was projected onto a reference photomultiplier tube (PMT, Hamamatsu Photonics, Japan) controlled by a time-correlated single photon counting (TCSPC) card (Becker & Hick! GmbH, Berlin, Germany) set to measure photon arrival times in a 25 ns window at a resolution of approximately 24 ps. This allowed the temporal pulse spread functions (TPSFs) of both laser pulses to be monitored during the experiment. The 96% output of the beamsplitter was coupled to fluorescence tomography imaging gantry and focused onto the center of the gantry where the imaging specimen was placed.

Opposite the excitation source on the gantry were five detection channels separated by 22.5° and focused to the center of the gantry. The collected signal at each of these five positions was separated into two channels, respectively, to monitor transmitted excitation light and fluorescent light, simultaneously. The filters employed in the fluorescence channels were custom designed multiple notch filters (Chroma Technologies, Bellows Falls, Vt.) having high attenuation in I 0-nm bandwidths centered at the two laser wavelengths to effectively remove excitation light from the path while allowing fluorescent light from both tracers to pass through to the TCSPC-controlled PMT detectors. The parameters of TCSPC detection of the fluorescence and transmittance TPSFs were the same as those employed for the reference PMT to allow the TPSFs from both lasers to be monitored. This allowed the temporal position of the TPSFs to be used to separate fluorescence from the different fluorophores in the imaging medium. The time-domain dual-wavelength data was split into separate signals by wavelength and processed independently. The system and all data were calibrated.

A 30-mm diameter cylindrical polymer phantom (INO, Quebec City, Canada) was constructed with optical properties to mimic tissue at near-infrared wavelengths. At excitation wavelength 755 nm, the refractive index of the phantom was 1.4, $\mu_a$=0.018 mm$^{-1}$, and $\mu_s'$=1.07 mm$^{-1}$. The phantom was constructed with three cylindrical inclusions running nearly the length of the phantom: one inclusion was 8 mm in diameter and the other two had a 4 mm diameter. The 8-mm diameter inclusion was filled with a combined 1:1 nM solution of IRDye 800CW (LI-COR Biosciences, Lincoln, Nebr.): Alexa Fluor 647 (Life Technologies, Grand Island, N.Y.) in 1% intralipid in water to provide a background type inclusion characteristic of a non-specific tracer accumulation in an organ of filtration. The bottom and right inclusions were filled with a 4:4 and an 8:4 nM ratio of the two tracers to represent inclusions with different levels of binding. The phantom was then imaged on the dual-wavelength fluorescent tomography system at 64 source positions about its circumference (corresponding to 320 source-detector pairs). Data were averaged for 5 s at each source position, yielding a total scan time of 12 min. NIRFAST reconstructions were carried out on the raw Born ratio data at the IRDye 800CW wavelength, the raw Born ratio data at the Alexa Fluor 647 wavelength, and using the dual-tracer background subtraction approach governed by Eq. 6 where the IRDye 800CW data was substituted for dT and the Alexa Fluor 647 data was substituted for $d_U$.

To test out the applicability of the dual-tracer background subtraction approach in an in vivo experiment, targeted and untargeted tracer concentrations were intravenously injected into an athymic mouse with a human glioma tumor implanted in its left cerebral hemisphere. The procedure for growing the tumor is discussed in detail elsewhere. The tumor line used in this study was a U25 1 human neuronal glioblastoma (provided by Dr. Mark Israel at Dartmouth College, Hanover, N.H.), which is known to overexpress the cell surface molecule, epidermal growth factor receptor (EGFR). In response, an EGFR-targeted tracer, IRDye 800CW-EGF (LI-COR Biosciences, Lincoln, Nebr.) was employed. The untargeted tracer was the same used in the phantom study. 2 nmol of both tracers was injected. The imaging and reconstructions were done in the same manner as described in Section 3.3 at 4 h post-injection, with the exception that the mouse imaging required removal of data projections that intersected with the mouse bed. Contrast-enhanced magnetic resonance imaging (MRI) was also carried out on the mouse to provide a secondary means of localizing the tumor mass, details of which have been discussed previously.

The results from the first simulation experiment wherein background fluorescence was incrementally increased in a circular imaging domain with two circular inclusions, while keeping contrast (inclusion fluorescence minus background fluorescence) the same and producing a reconstruction for each increase in background signal. It is clear that the quality of the fluorescence was exceedingly sensitive to the level of background fluorescence, with substantial artifacts appearing after the third image, corresponding to a 4:1 contrast-to-background ratio (CBR). The same experiment was repeated for an order of magnitude higher contrast (while keeping the CBRs the same) with no observed change (results not shown). This apparent sensitivity of fluorescence tomography background signal, independent of contrast is a significant limitation to fluorescence tomography. As such, a number of efforts have been made to mitigate background effects on fluorescence tomography by fitting autofluorescence spectra, subtracting pre-injection images from post-injection images, removing background fluorescence through analytical modeling, or constraining the reconstruction algorithms.

We demonstrated the utility of a simple background subtraction technique when using the homogeneous background subtraction approach on the data. The result was that both inclusions could be seen equally well for any level of background except for in the zero-background image, where the result was worse than the corresponding naive reconstruction. While the overall vast improvements in inclusion localization were obvious from comparing the background subtracted images with the raw-data based images in FIG. 2b, further discussion is warranted to explore the utility of the homogeneous background subtraction approach for in vivo applications. One component of the approach is that it requires optimization of the scaling factor, c. As discussed in the Theory section, c accounts for any scaling differences between the targeted tracer dataset and the background dataset (whether it is a forward model of homogenous background as in this case, or the distribution of a second untargeted tracer, discussed below). This parameter can be found relatively accurately if at least one source-data projection probes an area of the imaging domain that is relatively void of bound tracer (i.e., an area inhabited by only background fluorescence signal). For most fluorescence tomography studies this assumption will likely hold, since in the majority of cases, targeted fluorescence is used to highlight localized pathologies in a larger field of view (such as a small tumor). One potential problem with the methodology of choosing c, however, is highlighted by the failure of the background subtraction approach when the original dataset is void of background. This failure is owed to the inherent assumption that there is at least some small level of background; therefore, in the absence of background, a small amount of the signal is still subtracted, causing fluorescence data arising from the inclusion to be removed.

A second, more important component of the homogeneous background subtraction approach is the assumption that the background is homogeneous. If indeed the background fluorescence is homogenous, this approach is powerful since it is not specific to any imaging geometry and does not require a second tracer to be injected; however, the nature of in vivo background fluorescence may be more complex. Background fluorescence in the context of systemically injected targeted fluorescent tracers is comprised of two constituents, non-specific fluorophore uptake (i.e., fluorescence arising from fluorescent tracer concentrations that are not bound to the specific target of interest), and autofluorescence (i.e., fluorescence arising from endogenous fluorophores). While autofluorescence is a major problem in the visible spectrum, it becomes much less of an effect in the near-infrared wavelength range (600-1000 nm), where many new tracers are being developed to exploit this property as well as the relatively low absorption properties of tissue in this range. In fact, within the near-infrared spectrum, it is much more likely that the background fluorescence signal is predominantly comprised of non-specific tracer uptake. While this fact means that the non-specific tracer uptake>>autofluorescence assumption made to derive Eq. 6 is adequate, heterogeneities in biological tissue with respect to blood flow and vascular permeability mean that in vivo background fluorescence is likely quite heterogeneous.

To test out the effect a heterogeneous background could have on the homogeneous background subtraction approach, another set of simulated data was created on the fluorescent mesh. We demonstrated that the effect of the variable background renders it impossible for raw fluorescent data to be used to reconstruct the location of the inclusions of interest. Likewise, even the homogeneous background subtraction method was not optimal in the face of the heterogeneous background. However, when a distribution of a second, untargeted tracer was simulated, matching the variable background of the simulated targeted tracer distribution, the dual-tracer background subtraction approach was capable of effectively removing the variable background, making the bound fluorescent tracer inclusions visible. It should be noted that in this simulation, 10% differences in optical properties were used to create the targeted and untargeted tracer datasets, respectively, suggesting that the proposed dual-tracer background subtraction approach is insensitive to differences in optical properties at the necessarily different wavelengths needed to resolve two tracers, simultaneously. Furthermore, there will always be errors associated with estimates of optical properties for any given imaging domain; however, the results of this simulation take this possible error into account as well, suggesting that the "best guess" forward model matrix introduced in Eq. 5 is likely to be sufficient to reconstruct either tracer at its wavelength, independently, given that a Born ratio formulation would be used to suppress model error.

The results of the phantom study presented in FIG. S provide experimental support for the utility of the dual-tracer background subtraction approach. The phantom consisted of three inclusions with the largest used as an estimation of a background level with low and equal concentration of targeted and untargeted tracer, a second inclusion was an estimation of an organ of filtration with high but also equal concentrations of both tracers, and the third inclusion was an estimation of a target of interest, such as a tumor, with a very high concentration of targeted tracer and a high concentration of untargeted tracer. The high concentration of untargeted tracer would be expected in tumors because of the enhanced permeability and retention effect. The reconstructions of the targeted and untargeted tracer datasets on their own were determined. In both cases, all three inclusions were visible, which is not surprising since the background fluorescence of the phantom is negligible and therefore approximates the infinite contrast scenario. However, looking at the targeted fluorescence distribution, it is not clear which of the inclusions is the "tumor" inclusion. Only by applying the dual-tracer background subtraction approach could the "tumor" inclusion clearly be realized, demonstrating the ability of the approach to be used to remove heterogeneous background and large non-specific uptake, such as might be expected in organs of filtration (e.g., the liver or kidneys). A post-reconstruction difference image was carried out to compare to the result, but no scaling value could be found that did not result in significant edge artifacts (results not shown). This highlights the importance of carrying out the dual-tracer data differencing prior to reconstruction as opposed to after reconstructing both tracer distributions, independently.

The results of the proof-of-principle mouse imaging experiment were determined. The EGFR-targeted tracer distribution reconstruction and the untargeted tracer reconstruction and surprisingly, neither of the maps co-localized with the location of the EGFR-expressing tumor indicated by contrast-enhanced MRI. It was expected that both tracers would have some appreciable uptake in the tumor compared to the background; however, the data was collected within 4 h of injecting the tracers, which is much earlier than most studies would indicate for the background fluorescence to washout. Upon further investigation by numerical simulations, it was noted that the reconstructions were consistent with reconstructions from fluorescence maps having contrast less than 2:1, tumor: background. Despite the spurious results of the targeted and untargeted tracer distributions on their own, the obvious recovered inclusion using the dual-tracer background subtraction approach matched well with the known location of the glioma, highlighting the power of this approach even when a very low contrast to background ratio is expected.

Planar Resolution of Fluorescent Agents in Tissue

In another experimental embodiment, an optical system similar to that of FIG. 2A, was tested using a mouse model. A human glioma was grow in an immune-deficient mouse, and first and second contrast agents administered 202, 204. The second or untargeted fluorescence agent was a carboxylate form of IRDye 700DX NHS Ester; LI-COR Biosciences, Lincoln, Nebr., and the first or targeted contrast agent was an EGFR-targeted fluorescence reporter IRDye 800CW EGF; LI-COR Biosciences, Lincoln, Nebr. The mouse was then placed in cavity 119A with tissue covering the glioma dissected away to expose the glioma. A first image was captured 208 of the first contrast agent in the glioma and surrounding tissue as illuminated by a scanned-laser stimulus source operating at a first stimulus wavelength. A second image was captured 212 of the second contrast agent in the glioma and surrounding tissue as illuminated by a scanned-laser stimulus source operating at a second stimulus wavelength. The second image was then scaled and subtracted from the first image to provide a corrected image. The corrected image was found to provide better contrast between glioma and surrounding tissue. Corrected images captured within 20 minutes of administration of the fluorescent contrast agents were found to resolve the glioma, where much longer delays between administration and imaging were required without the dual-agent, background subtraction, method herein described.

CONCLUSION

It is noted that both the targeted or selective first contrast agent and the untargeted or unselective second contrast agent of each tracer pair used should have similar transport kinetics (i.e., vascular permeability), similar plasma pharmacokinetics, and similar levels of nonspecific uptake and binding in tissue. The present system is particularly suited for use with fluorophores having emissions light spectra in the near-infrared range.

It is anticipated that the dual-agent, background subtraction, method herein described may operate with any combination of the described stimulus light sources, for example but not limitation the optical path of FIG. 1 is expected to be operable with scanned-laser light sources, and the optical path of FIG. 2A may provide planar images using unscanned, filtered, light sources or light emitting diodes.

It is anticipated that the dual-agent, background subtraction, fluorescent imaging method herein described may be adapted to performing both planar fluorescent imaging, and to performing fluorescent tomographic imaging with appropriate optical systems and image postprocessing.

It is anticipated that the fluorescent imaging system herein described may be combined with tracking systems for determining precise relative locations of the optical system and a subject, the tissue being located in the subject; and adapted to register fluorescent images with white light images, and to register those images with preoperative CT and/or MRI images. In particular, it is anticipated that the fluorescent imaging system may be adapted to use an optical system of a stereo operating microscope that is equipped with intraoperative stereovision surface mapping and tissue- and-tumor-displacement modeling features as described in PCT/US PCT/US13/24400, such that intraoperative fluorescent images may be compared with preoperative CT and MRI images that have been corrected for intraoperative tissue displacement, such that a surgeon may ensure complete removal of tumor tissue as seen in preoperative imaging, as well as in intraoperative fluorescent images.

Combinations

It is anticipated that the systems herein described may be implemented with various combinations of features, and used with various pairs of differing fluorophores. Some of those anticipated combinations are as follows:

A system designated A for generating corrected fluorescence data of concentrations of a targeted fluorophore in tissue of a subject, includes apparatus configured for illuminating tissue with light of a first stimulus wavelength; and for illuminating tissue with light of a second stimulus wavelength. The system also has photodetector apparatus adaptable to capture a first data at a first emissions wavelength while tissue is illuminated with light of the first stimulus wavelength, and to capture a second data at a second emissions wavelength while tissue is illuminated with light of the second stimulus wavelength, and an image processing system with a memory configured to store the first data and second data and a processor. At least the first and second emissions wavelengths are different wavelengths. The processor is configured with machine readable code in the memory to scale at least one of the first and second data, and to generate difference data by subtracting the second data from first data.

A system designated AA including the system designated A wherein the first and second data, and the difference data, are digital images.

A system designated AB including the system designated A or AA wherein the first and second stimulus wavelength are different wavelengths.

A system designated AC including the system designated AA wherein the first data represents data acquired by at least one multichannel photodetector with the tissue illuminated at each of a plurality of discrete points in succession, the machine readable code further comprises instructions for reconstructing a first three dimensional model of first fluorophore distribution in tissue from the first data, and a second three dimensional model of second fluorophore distribution in tissue from the second data, and the instructions for deriving the difference data operate by differencing voxels of the first and second three dimensional models.

A system designated ACA including the system designated A, AA, AB, or AC further comprising apparatus configured for administering a contrast agent, the apparatus configured for administering a contrast agent containing a contrast agent including a first contrast agent comprising a substance consisting of substance selected from the group consisting of a prodrug metabolizable into a first fluorophore and a tissue-selective agent comprising a first fluorophore; and a second contrast agent comprising a second fluorophore; wherein the first fluorophore emits light of the first emissions wavelength when stimulated by light of the first stimulus wavelength, and the second fluorophore emits light of the second emissions wavelength when stimulated by light of the second stimulus wavelength.

A system designated ACB including the system designated ACA wherein the first contrast agent comprises a prodrug metabolizable into the first fluorophore.

A system designated ACC including the system designated ACA wherein the first contrast agent comprises a fluorescent-labeled antibody.

A system designated AD including the system designated A, AA, AB, AC, ACA, ACB, or ACC further comprising in the memory superposition routines adapted for superimposing the difference data on a white-light image.

A method designated B of generating corrected fluorescence data of concentrations of a targeted fluorophore in tissue of a subject, including: administering a first fluorescent contrast agent to the subject, the first contrast agent selected from the group consisting of tissue-targeted agents containing the targeted fluorophore and agents containing a tissue-targeted prodrug metabolizable by tissue into the targeted fluorophore; and administering a second fluorescent contrast agent to the subject, the second contrast agent containing a second fluorophore and having tissue affinity differing from that of the first contrast agent. The method continues with illuminating tissue of the subject with light of a first stimulus wavelength; acquiring first data at a first emissions wavelength associated with the targeted fluorophore; and acquiring second data at a second emissions wavelength associated with the second fluorophore, the second emissions wavelength different from the first emissions wavelength. Once the data is acquired, the method includes subtracting the second data from the first data to provide the corrected fluorescence data. The method assumes that the first fluorophore emits light of the first emissions wavelength when stimulated by light of the first stimulus wavelength, and the second fluorophore emits light of the second emissions wavelength when stimulated by light of the second stimulus wavelength.

A method designated BA including the method designated B wherein each of the first data, second data, and corrected fluorescence data, are digital images.

A method designated BB including the method designated B wherein the first data represents data acquired by a multichannel photodetector with the tissue illuminated at each of a plurality of points, and further comprising reconstructing a tomographic model of fluorophore distribution in the tissue.

A method designated BC including the method designated B, BA, or BB, further comprising scaling at least one member of the group consisting of the second data and the first data prior to the step of subtracting.

A method designated BD including the method designated B, BA, BB, or BC wherein the first and second emissions wavelengths are different.

A method designated BE including the method designated B, BA, BB, BC or BD wherein the first and second stimulus wavelengths are different.

A method designated BF including the method designated B, BA, BB, BC, BD, or BE wherein the first contrast agent comprises a prodrug metabolizable into the first fluorophore.

A method designated BG including the method designated B, BA, BB, BC, BD, or BE wherein the first contrast agent comprises a fluorescent-labeled antibody.

A method designated BI including the method designated B, BA, BB, BC, BD, BE, BF, or BG and further including obtaining a white-light image, and superimposing the corrected difference data on the white-light image.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for generating three dimensional images of bound fluorophore concentrations in tissue from difference data of the fluorescence response of a nontargeted fluorophore subtracted from the fluorescence response of a targeted fluorophore, the targeted and nontargeted fluorophores being different, comprising:
    a first apparatus configured for generating and illuminating tissue with light selectable between a nontargeted stimulus wavelength and a targeted stimulus wavelength;
    photodetector apparatus adaptable to capture nontargeted emissions data at a nontargeted set of emission wavelengths while the tissue is illuminated with light of the nontargeted stimulus wavelength, and to capture targeted emissions data at a targeted set of emission wavelengths while tissue is illuminated with light of the targeted stimulus wavelength, where at least the nontargeted and targeted stimulus wavelength are different wavelengths, and the nontargeted and targeted emissions wavelengths are different wavelengths;
    a memory configured to store the nontargeted emissions data and the targeted emissions data;
    a processor configured with machine readable code in the memory;
        the machine readable code comprising instructions for reconstructing bound fluorophore concentrations of a voxel-based three dimensional model of distribution of bound targeted fluorophore concentration in tissue from difference data derived by subtracting the nontargeted emissions data from the targeted emissions data.

2. The system of claim 1 further comprising apparatus configured for administering a contrast agent, the apparatus configured for administering a contrast agent containing a contrast agent comprising:
    a first contrast agent comprising a substance selected from the group consisting of a prodrug metabolizable into a targeted fluorophore and a tissue-selective agent comprising a targeted fluorophore; and
    a second contrast agent comprising a nontargeted fluorophore;
    wherein the first fluorophore emits light of the targeted emissions wavelength when stimulated by light of the targeted stimulus wavelength, and the nontargeted fluorophore emits light of the nontargeted emissions wavelength when stimulated by light of the nontargeted stimulus wavelength.

3. The system of claim 2 wherein the first contrast agent is a prodrug metabolizable into the targeted fluorophore.

4. The system of claim 1 wherein the machine readable code comprises instructions to scale an emissions data selected from the group selected from the nontargeted emissions data and the targeted emissions data prior to subtracting the nontargeted emissions data from the targeted emissions data.

* * * * *